United States Patent [19]

Warriner

[11] Plant 3,994

[45] Dec. 21, 1976

[54] ROSE PLANT

[75] Inventor: William A. Warriner, Tustin, Calif.

[73] Assignee: Jackson & Perkins Company, Medford, Oreg.

[21] Appl. No.: 622,905

[22] Filed: Oct. 16, 1975

[51] Int. Cl.[2] ..... A01H 5/00

[52] U.S. Cl. ..... Plt./28

[58] Field of Search ..... Plt./28–29

*Primary Examiner*—Robert E. Bagwill

*Attorney, Agent, or Firm*—Klarquist, Sparkman, Campbell, Leigh, Hall & Whinston

CLAIM

A new and distinct cultivar of rose plant, substantially as herein shown and as described, characterized particularly as to novelty by its similarity to the parent cultivar, Marlena, U.S. Plant Pat. No. 2,700, but differing from Marlena in that in the subject cultivar the receptacle is quite glandular having a funnel-like shape with a broad distal end, the anthers being of a darker yellow, the filaments being shorter, the stigmas being of Uranium Green (6 3/2) W and protruding further than the anthers.

1 Drawing Figure

The present invention relates to a new and distinct cultivar of rose plant of the floribunda class which was originated by me by crossing the cultivar Marlena, U.S. Plant Pat. No. 2,700 with pollen from an unnamed cultivar of the hybrid tea class.

The primary objective of this breeding was to produce a new cultivar of the compact floribunda class similar to the parent cultivar, Marlena, that would have similar growth and color and that would, under most conditions, be more resistant to effects of mildew such that foliage would be held on the plant throughout the growing season. This objective was fully achieved along with other technical botanical differences, as evidenced by the following unique combination of characteristics which are outstanding in the new cultivar and which distinguish it from its parents as well as from all other cultivars of which I am aware:

1. A compact, well branched plant reading approximately 20" to 24" in height, when grown at Irvine, Calif., after 2 years growth.

2. A flower color near Cardinal Red at all stages of opening.

3. The following morphological differences between this new cultivar (designated 68-6975 in the breeding records) and the parent cultivar Marlena:

| 68-6975 | Marlena |
|---|---|
| Receptacle is quite glandular. | Receptacle has few glands. |
| Receptacle shape is funnel-like with a broad distal end. | Receptacle is more apple-shaped, with the distal end narrower than the middle. |
| Anthers are darker yellow than Marlena. | |
| Filaments shorter than Marlena. | |
| Stigmas protrude farther than anthers. | Anthers protrude farther than stigmas. |
| Stigmas are Uranium Green (63/2)W | Stigmas are Ivory Yellow, Pl. 30 R. |

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development depicted in color as nearly true as it is reasonably possible to make the same in a color illustration of this character.

The following is a detailed description of my new rose cultivar with color terminology in accordance with Wilson's Horticultural Color Chart (W) and Ridgway — Color Standards & Nomenclature (R), except where ordinary dictionary significance of color is indicated.

Parentage: Seedling

*Seed Parent.*—Marlena, U.S. Plant Pat. No. 2,700.

*Pollen Parent.*—Unnamed cultivar.

Classification:

*Botanical.*—Rosa hybrid.

*Commercial.*—Floribunda.

FLOWER

Observations made from specimens grown at Irvine, Calif., September 1975.

Blooming habit: Continuous.

Bud:

*Size.*—½" to ¾" when petals start to unfurl.

*Form.*—Short, blunt top.

*Color.*—When sepals first divide—near Cardinal Red (822)W. When half blown; upper side of petals near Cardinal Red (822/3)W, lower side of petals near Chrysanthemum Crimson (824/3)W.

*Sepals.*—Color: Outer surface near Scheeles Green (860)W with an overcast of Garnet Brown (00918/3)W. Inner surface near Scheeles Green (860)W with a light covering of white tomentum. Three appendaged sepals lightly, appendaged. Two unappendaged sepals, hairy edged.

*Receptacle.*—Color near Scheeles Green (860)W, overcast with Garnet Brown (00918/3)W. Shape: funnel. Size: large, broad. Surface: slightly glandular.

*Peduncle.*—Length: short. Surface: glandular stipitate glands. Color: light green. Strength: stiff, erect.

*Opening.*—Petals fold out flat with little or no recurvins of petal tips or edges.

Bloom:

*Size.*—Small. Average open size 2" to 2½".

*Borne.*—Singly and in flat clusters.

*Stems.*—Short, strong.

*Form.*—When first open, flat. Permanence: retains its form to the end.

*Petalage.*—Number of petals under normal conditions 25–30.

*Color.*—Upper side of petals: Near Cardinal Red (822/3)W. Reverse side of petals: Near Chrysanthemum Crimson (824/3)W. Base of petals: Small area near white. General tonality from a distance: Cardinal Red (822/3)W. Variegations, if any: Occasional white centerline on some petals and petaloids.

*Discoloration.*—General tonality at end of first day: No change. Third day: Color is same hue but has less gloss, appears slightly grayed.

*Fragrance.*—Slight.

Petals:

*Texture.*—Leathery, stiff.

*Shape.*—Oval, slightly notched.

*Form.*—Flat.

*Arrangement.*—Loosely imbricated. Petaloids in center: Few.

*Persistence.*—Drop off cleanly.

*Lastingness.*—On the plant: Long. As cut flower: Long.

Reproductive parts:

*Anthers.*—Large, many. Color: Light Orange yellow, Pl. III R. Arrangement: Regular around styles.

*Filaments.*—Shorter than those on Marlena. Color: Light Orange yellow, Pl. III R, with overcast of varying pink shades.

*Pollen.*—Gold yellow.

*Styles.*—Color: Near Uranium Green (63/2)W.

*Stigmas.*—Color: Near Uranium Green (63/2)W.

PLANT

Form: Bush.

Growth: Vigorous, upright, branching. Very compact plant to approximately 24" in height and width.

Foliage: Number of leaflets on normal mid-stem leaves: 5

*Size.*—Medium.

*Quantity.*—Normal.

*Color.*—New foliage: Near Garnet Brown (00918/3)W. Old foliage: Near Parsley Green (00962)W.

*Shape.*—Oval pointed.

*Texture.*—Upper side: leathery.

*Edge.*—Serrated, slightly undulated.

*Serration.*—Single; small.

*Petiole.*—Rachis: Color, green. Underside: prickles.

*Stipules.*—Medium, slightly bearded.

*Disease Resistance.*—Normally resistant to mildew under normal growing conditions at Irvine, Calif.

Wood:

*New Wood.*—Color: light green. Bark: Smooth.

*Old Wood.*—Color: green. Bark: Smooth.

Prickles:

*Quantity.*—On main stalks from base: many. On laterals from stalk: many.

*Form.*—Broad base, hooked downwardly.

*Color when young.*—Red to brown.

*Position.*—Irregular.

Small Prickles:

*Quantity.*—On main stalks: few. On laterals: few.

*Color.*—Brown.

I claim:

1. A new and distinct cultivar of rose plant, substantially as herein shown and as described, characterized particularly as to novelty by its similarity to the parent cultivar, Marlena, U.S. Plant Pat. No. 2,700, but differing from Marlena in that in the subject cultivar the receptacle is quite glandular having a funnel-like shape with a broad distal end, the anthers being of a darker yellow, the filaments being shorter, the stigmas being of Uranium Green (6 3/2) W and protruding further than the anthers.

* * * * *

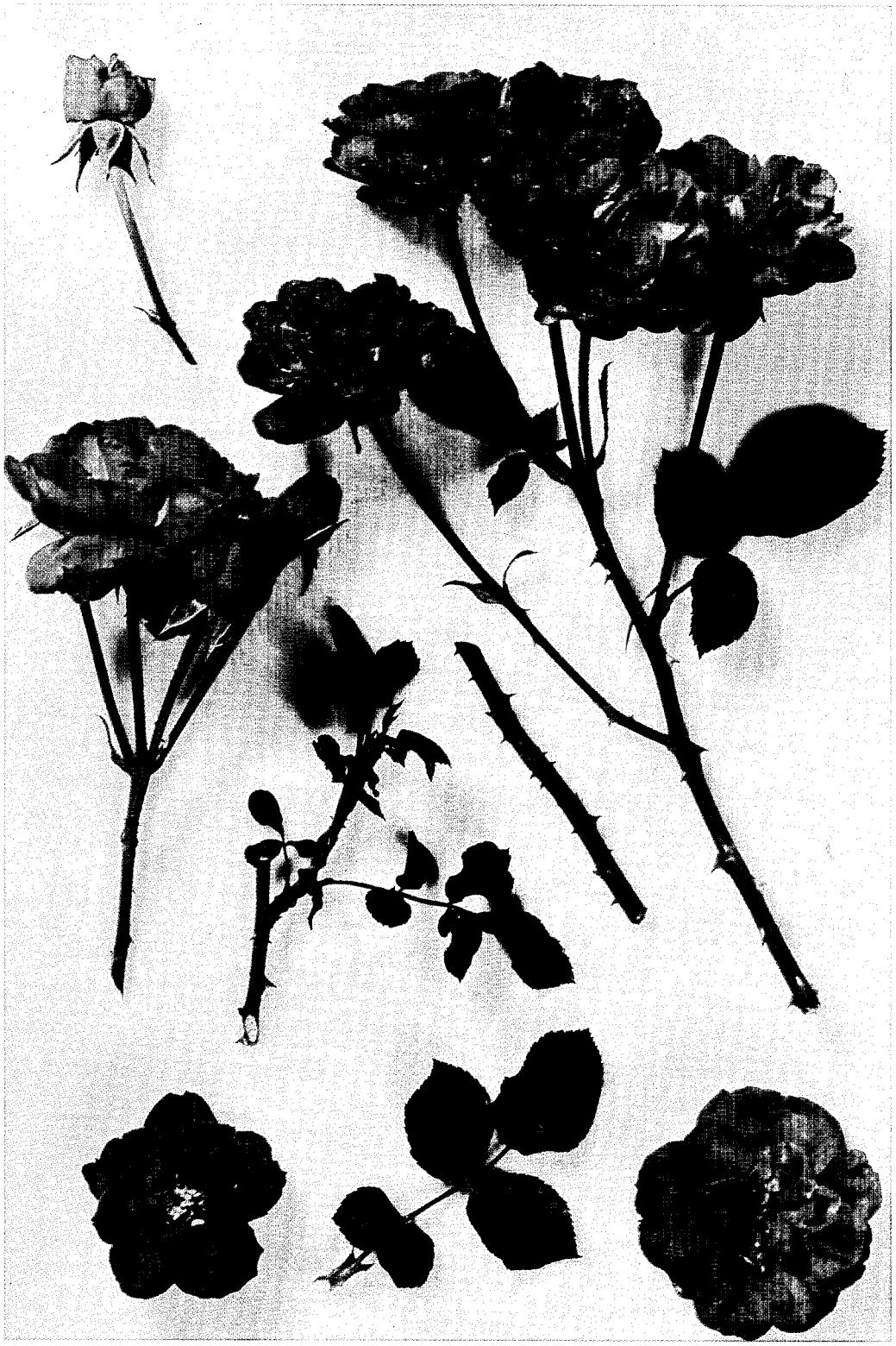

Dec. 21, 1976 W. A. WARRINER Plant Pat. 3,994
ROSE PLANT
Filed Oct. 16, 1975